United States Patent
MacDougald et al.

(10) Patent No.: US 7,282,195 B2
(45) Date of Patent: Oct. 16, 2007

(54) FLAVORED SEALANTS

(76) Inventors: Ian T. MacDougald, 23 Silo Hill Rd., Madison, CT (US) 06443; Weitao Jia, 73 Liney Hall La., Wallingford, CT (US) 06492

( * ) Notice: Subject to any disclaimer, the term of this patent is extended or adjusted under 35 U.S.C. 154(b) by 225 days.

(21) Appl. No.: 10/410,848

(22) Filed: Apr. 10, 2003

(65) Prior Publication Data

US 2004/0202620 A1 Oct. 14, 2004

(51) Int. Cl.
- *A61K 8/18* (2006.01)
- *A61K 8/97* (2006.01)
- *A61K 8/02* (2006.01)
- *A61K 9/50* (2006.01)

(52) U.S. Cl. .......................... 424/49; 424/58; 424/401; 424/501

(58) Field of Classification Search ................. 424/49, 424/58, 401, 501; 106/35; 523/118; 433/226, 433/228.1
See application file for complete search history.

(56) References Cited

U.S. PATENT DOCUMENTS

| | | | |
|---|---|---|---|
| 3,943,241 A | | 3/1976 | Anderson |
| 4,940,676 A * | | 7/1990 | Evans .......................... 501/16 |
| 5,367,002 A | | 11/1994 | Huang |
| 5,444,104 A * | | 8/1995 | Waknine ........................ 522/24 |
| 5,922,785 A * | | 7/1999 | Waller et al. ................ 523/116 |
| 6,030,606 A * | | 2/2000 | Holmes ......................... 424/49 |
| 6,270,562 B1 * | | 8/2001 | Jia ................................ 106/35 |
| 6,342,204 B1 | | 1/2002 | Combe |
| 6,419,904 B1 | | 7/2002 | Combe |
| 6,444,253 B1 | | 9/2002 | Conklin et al. |
| 6,444,725 B1 * | | 9/2002 | Trom et al. .................. 523/118 |
| 6,451,295 B1 | | 9/2002 | Warford |
| 6,455,608 B1 * | | 9/2002 | Jia et al. ...................... 523/115 |
| 6,534,042 B2 | | 3/2003 | Santi et al. |
| 6,620,859 B2 * | | 9/2003 | Warford et al. ............. 523/115 |
| 6,730,156 B1 * | | 5/2004 | Windisch et al. ............. 106/35 |
| 2001/0006623 A1 | | 7/2001 | Warford |
| 2002/0012638 A1 | | 1/2002 | Warford |
| 2002/0018756 A1 | | 2/2002 | Warford |
| 2002/0077382 A1 | | 6/2002 | Warford |
| 2002/0106334 A1 | | 8/2002 | Combe |
| 2002/0156152 A1 | | 10/2002 | Zhang |
| 2002/0198282 A1 * | | 12/2002 | Jia .............................. 523/115 |
| 2003/0003059 A1 | | 1/2003 | Dana |
| 2003/0004294 A1 | | 1/2003 | Moszner |
| 2003/0018098 A1 | | 1/2003 | Falsafi |

OTHER PUBLICATIONS

Code of Federal Regulations—21 CFR § 21 182.20, (2003).
Code of Federal Regulations—21 CFR § 172.515, (2003).

* cited by examiner

*Primary Examiner*—Raymond J. Henley, III

(57) ABSTRACT

A single-component composition for repairing, protecting or sealing teeth comprising a polymerizable resin, a flavoring agent, wherein the flavoring agent is a non-oil containing natural flavoring agent, or an artificial flavoring agent, an ultraviolet light absorber, a curing system, and optionally a filler.

22 Claims, No Drawings

FLAVORED SEALANTS

FIELD OF THE INVENTION

The present invention relates generally to compositions for repairing, protecting and sealing teeth, and more specifically to flavored sealants for repairing, protecting and sealing teeth.

BACKGROUND OF THE INVENTION

Patient comfort is important to both the individual patient being treated and the dental professional performing the treatment. More particularly, when the patient is a child, a patient that is comfortable and relaxed is much less likely to move in a manner so as to make the treatment more difficult for the dental professional to perform. Additionally, a comfortable patient is more likely to take the direction of the dental professional during the treatment, and further, to adhere to any prescribed regimens post-treatment. However, although many new materials and/or procedures have been provided, or existing materials and procedures improved, that enhance patient comfort, i.e., such as improvements in anesthetic materials and the development of more comfortable tooth preparation procedures, there still exist areas within the field of dentistry in which patient comfort could be further enhanced or optimized.

Many of the materials used by the dental professional are not pleasing to the sensory palate. The materials are bitter tasting and smelling and leave an unpleasant aftertaste in the patient's mouth, which may be particularly problematic when the patient being treated is a child. Many children are treated with pit and fissure sealants having an offensive odor and flavor, creating discomfort to the child during the application of the sealant.

In order to enhance the patient's experience, and in keeping with the general trend of making dentistry more acceptable for patients, it would be desirable to at least reduce or eliminate the unpleasant flavor associated with sealant materials, and would be even more desirable to provide such materials with a pleasant flavor while also beneficially imparting such materials with a pleasing aroma. It would be beneficial to provide a one-component sealant for ease and simplicity of application.

SUMMARY OF THE INVENTION

These and other objects and advantages are accomplished by a single-component dental composition for use in repairing, protecting or sealing teeth. The composition includes a natural or artificial flavoring agent or mixture thereof to provide a pleasant tasting and smelling material for application on a patient's teeth. The flavoring agent is a non-oil containing material to prevent a persistent aftertaste in a patient's mouth long after treatment has been performed.

DETAILED DESCRIPTION OF THE PREFERRED EMBODIMENTS

The present invention provides dental compositions for repairing, protecting and sealing teeth that comprise one or more additives for providing a pleasing flavor to the dental composition. The dental compositions preferably comprise a polymerizable resin, a flavoring agent, along with a curing additive or system, and an ultraviolet light absorber. It is preferable to have a one-component sealant, although two-component self-curing sealants may also be provided. Other additives may be included in the composition including but not limited to fillers, fluorides, antimicrobial agents, and pigments.

The polymerizable resin preferably comprises acrylate or methacrylate resins. Typical acrylate resinous materials useful herein are disclosed in U.S. Pat. No. 3,066,112 to Bowen, U.S. Pat. No. 3,179,623 to Bowen, U.S. Pat. No. 3,194,784 to Bowen, U.S. Pat. No. 3,751,399 to Lee et al., U.S. Pat. No. 3,926,906 to Lee et al., and commonly assigned U.S. Pat. Nos. 5,276,068 and Pat. No. 5,444,104 to Waknine, all of which are incorporated herein by reference. Other resin materials include, but are not limited to, urethane dimethacrylate (UDMA), diurethane dimethacrylate (DUDMA), and other monomers and oligomers known in the art. A useful oligomer is disclosed in U.S. Pat. Nos. 5,276,068 and U.S. Pat. No. 5,444,104 to Waknine, being a polycarbonate dimethacrylate (PCDMA) which is the condensation product of two parts of a hydroxyalkylmethacrylate and 1 part of a bis(chloroformate). Another advantageous resin having lower water sorption characteristics is an ethoxylated bisphenol A dimethacrylate (EBPDMA) as disclosed in U.S. Pat. No. 6,013,694. More examples include, but are not limited to, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates, triethylene glycol dimethacrylate (hereinafter abbreviated "TEGDMA"), polyethylene glycol dimethacrylate (hereinafter abbreviated "PEGDMA"), urethane dimethacrylate (hereinafter abbreviated "UDMA"), hexane diol dimethacrylate (hereinafter abbreviated "1,6 HDDMA") and polycarbonate dimethacrylate (hereinafter abbreviated "PCDMA") and the like. Among the examples given, the resins containing surface functional groups such as acrylate/methacrylate, epoxy, hydroxyl and others are preferred. Examples of polymeric matrix materials based on acrylic and methacrylic monomers, are disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. Nos. 5,276,068 to Waknine (which are herein incorporated by reference). Preferred methacrylate monomers include is the condensation product of bisphenol A and glycidyl methacrylate, 2,2'-bis [4-(3-methacryloxy-2-hydroxy propoxy)-phenyl]-propane (hereinafter abbreviated "BIS-GMA"), tetrahydrofurfuryl methacrylate (THFMA), ethoxylated bisphenol A dimethacrylate (EBPADMA), 1,6-hexanediol dimethacrylate (HDDMA) and hydroxyethyl methacrylate (HEMA). Especially preferred monomers include a mixture of a high viscosity monomer such as BIS-GMA and a low viscosity monomer such as TEGDMA or THFMA. The resin or resin mixture is present in an amount of from about 50 to about 98 percent by weight of the composition.

The flavoring agent may be a natural or artificial flavoring agent. Natural flavoring agents may include an oleoresin, essence, extractive, protein hydrolysate, distillate of any product of roasting, heating or enzymolysis, which contains the flavoring constituents derived from a spice, fruit juice, vegetable or vegetable juice, herb, bud, bark, root, leaf or similar plant material, and mixtures thereof. Natural solvents, carriers and emulsifiers may be added. It is preferable to use a flavoring agent in the form of a non-oil containing extractive.

Examples of natural flavoring agents include, but are not limited to, cinnamon, ginger, lemon, orange, grape, carob bean, cherry, cherry, banana, apple, berry, chicory and cola. Natural extractives which may be used in natural flavoring agents herein and which have been approved by the Food and Drug Administration are listed in FDA Regulation 21 CFR 182.20, which is hereby incorporated by reference.

Preferably, artificial flavoring agents are used due to the ability of the flavoring agent to dissipate after a short period of time. During application of the sealant containing the artificial flavoring agent, the flavoring agent will compensate for the undesirable taste of the resins contained in the sealant, but will not persist for a long period of time, i.e., less than an hour after the period of treatment, and preferably no longer than the time period of treatment. Natural flavoring agents containing essential oils can be found to have a persistent flavor due to the immiscibility in water and are not recommended for use herein.

Artificial flavoring agents are preferably in the form of hydrocarbons, alcohols, aldehydes, ketones, esters, phenol ethers, lactones, quinones, and various organic acids, singly or in combination. Examples include, but are not limited to, anisyl alcohol (caramel), benzyl cinnamate (chocolate), vanillin acetate (vanilla), decyl acetate (orange), 2-methylbutyaldehyde (coffee), allyl propionate (apple), perillaldehyde (cherry), and carvyl acetate (peppermint). Artificial flavoring agents may be blended with natural flavoring agents. Artificial flavoring agents useful herein are listed in FDA Regulation 21 CFR 172.515, which is hereby incorporated by reference. The flavoring agent is present in an amount from about 0.01 to about 5 percent by weight, or from about 0.05 to about 2 percent by weight of the composition.

In addition to the above polymerizable resins and flavoring agents, the dental materials also typically contain curing systems and other additives, e.g., polymerization initiators, polymerization accelerators, ultraviolet light absorbers, antioxidants, and other additives well known in the art. For example, visible light polymerizable compositions employ light-sensitive compounds, including, but not limited to, benzil, benzoin, benzoin methyl ether, ethyl (4-dimethylamino)benzoate (EDMAB), DL-camphorquinone (CQ) and benzil diketones. Either UV-activated cure or visible light-activated cure (approx. 230 to 750 nm) is acceptable. The amount of photoinitiator is selected according to the cure rate desired. A minimal catalytically effective amount is generally about 0.01 wt. % of the total resin composition, and will lead to a slower cure. Faster rates of cure are achieved with amounts of catalyst in the range from greater than about 0.01% to about 5 percent by weight of the composition. Alternatively, the composition may be formulated as a self-curing system. Self-curing compositions will generally contain free radical polymerization initiators such as, for example, a peroxide in amounts of about 0.05 to about 3.0 wt % of the total resin composition. Particularly suitable free radical initiators are lauryl peroxide, tributyl hyperoxide and, more particularly benzoyl peroxide. It is preferred to employ light-sensitive compounds so that visible light can be used to cure the dental restorative composition.

Polymerization accelerators suitable for use are the various organic tertiary amines well known in the art. In visible light polymerizable compositions, the tertiary amines are generally acrylate derivatives such as dimethylaminoethyl methacrylate and, particularly, diethylaminoethyl methacrylate (DEAEMA) in amounts of about 0.05 to about 0.5 wt. % of the total resin composition. In self-curing compositions, the tertiary amines are generally aromatic tertiary amines, preferably tertiary aromatic amines such as ethyl 4-(dimethylamino)benzoate (commonly known as "EDMAB"), 2-[4-(dimethylamino)phenyl] ethanol, N,N-dimethyl-p-toluidine (commonly abbreviated "DMP"), bis (hydroxyethyl)-p-toluidine, and treithanaolamine and are generally present in amounts of about 0.5 to about 4.0 wt. % based on the resin composition.

Ultraviolet light absorbers are particularly desirable in the visible light polymerizable compositions in order to avoid discoloration of the resin from any incident ultraviolet light. Suitable ultraviolet light absorbers are, for example, benzophenones such as 2-hydroxy-4-methoxybenzophenone, benzotriazoles, such as 2-(2'-hydroxy-5'-methylphenyl)benzotriazole sold under the trademark TINUVIN P by Ciba-Geigy Corporation, Ardsley, N.Y., 2-(2-hydroxy-5-tert-octylphenyl)benzotriazole (available under the trade name UV-54 from American Cyanamid Company) and other derivatives thereof, in amounts ranging from about 0.01 to about 5.0 percent by weight.

A filler component may optionally be added and may include any known filler in the art of dental materials including, but not limited to, an inorganic calcium-containing compound, for example, calcium hydroxide, calcium phosphates, tricalcium phosphate, or calcium oxide, inorganic and organic particulates and fibrous fillers known in the art, such as particulate poly(lactide), poly(glycolide), poly(lactide-co-glycolide) or poly(methacrylate), or particulate or fibrous silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania. The filler component may be added in an amount of up to about 50 percent by weight.

The above-mentioned components, i.e., the polymerizable resins, flavoring agents, polymerization initiators and accelerators, and fillers may be provided to the practitioner as a one-part or two-part system. In the one-part system, the curing reaction may be triggered shortly before usage in dental restorative applications by the utilization of visible light, UV light or increased temperature.

Optionally, the various components forming the dental restorative composition may be divided into two parts, with a first part comprising, for example, a portion of the polymerizable resin and optional fillers and the second part containing the remaining portion of the polymerizable resin along with polymerization initiators, accelerators, other reactive optional fillers, and the like. When the two-part system is used as a dental restorative, the two parts are mixed thoroughly before use.

The various embodiments of the disclosure are further illustrated by the following non-limiting examples.

EXAMPLES

Flavoring agents were added to two commercially available sealants, Protect-It® Sealant and Flow-It® flowable composite, available from Pentron Clinical Technologies, LLC, Wallingford, Conn., and the presence of the scent was measured immediately after curing and after two days of submersion in water. Table 1 sets forth the following results.

TABLE 1

| Example | Sealant | Flavoring Agent (wt %) | Scent present before curing | Scent present right after curing | Scent present after cured material submerged in water for 2 days at 37° C. |
|---|---|---|---|---|---|
| Example 1 | Protect-It ® | none | offensive odor from the material itself | almost none | none |
| Example 2 | Protect-It ® | 0.5% vanilla flavor[1] | vanilla | vanilla | none |
| Example 3 | Protect-It ® | 0.2% chocolate flavor[2] | chocolate | chocolate | none |
| Example 4 | Protect-It ® | 0.5% wild berry[3] | berry | berry | none |
| Example 5 | Flow-It ® | 0.3% peppermint essential oil | mint | mint | detectable mint |
| Example 6 | Flow-It ® | none | light odor (ester-like) | none | none |
| Example 7 | Flow-It ® | 0.5% vanilla flavor[1] | vanilla | vanilla | none |
| Example 8 | Flow-It ® | 0.2% chocolate flavor[2] | chocolate | chocolate | none |
| Example 9 | Flow-It ® | 0.5% wild berry[3] | berry | berry | none |
| Example 10 | Flow-It ® | 0.3% peppermint essential oil | mint | mint | detectable mint |

[1]Natural and Artificial Flavor #2120 from Target Flavors, Inc., Brookfield, Connecticut
[2]Chocolate Flavor #5428 from Target Flavors, Inc.
[3]From Carrubba Inc., Milford, CT From the results shown in Table 1, it can be seen that the artificial flavors are undetectable after two days of submersion in water in comparison to the essential oil of peppermint used in Examples 5 and 10.

Water sorption and solubility tests were conducted according to ISO 4049 for dental resin-based composite materials on Examples 5 through 10. The results are shown in Table 2.

TABLE 2

| Example | Water Sorption (µg/mm3) | Solubility (µg/mm3) |
|---|---|---|
| 6 | 13.0 | 6.5 |
| 7 | 14.5 | 8.3 |
| 8 | 13.3 | 5.4 |
| 9 | 15.7 | 6.5 |
| 10 | 10.5 | 5.3 |

From the results, it appears that the artificially-flavored materials have similar or slightly higher water sorption than the original material. The material containing peppermint oil, however, shows less water sorption.

The experiments have successfully demonstrated the objective of using a flavoring agent for temporarily relieving the sensory effects of a dental material without causing adverse affects on the material by avoiding a persistent aftertaste in a patient's mouth after treatment.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of sealing a patient's teeth with a sealant comprising:
    applying a single-component sealant to a patient's teeth wherein the single-component sealant composition for protecting or sealing teeth comprises:
        about 50 to about 98% by weight of a polymerizable resin;
        about 0.01 to 0.5% by weight of a flavoring agent, wherein the flavoring agent is selected from the group consisting of a non-oil containing natural flavoring agent, an artificial flavoring agent, and mixtures thereof, whereby the flavoring agent is selected based on its detectability wherein the flavoring agent in a cured dental sealant has a scent that is undetectable by a patient after two days of submersion in water at 37° C.;
        about 0.01 to about 5% by weight of an ultraviolet light absorber;
        about 0.01 to about 5% by weight of a curing system; and optionally up to about 50% by weight of a filler; and
curing the sealant.

2. The method of claim 1 wherein the polymerizable resin comprises a resin selected from the group consisting of acrylate, methacrylate, polyamides, polyester, polyolefins, polyimides, polyarylates, polyurethanes, vinyl esters, epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates.

3. The method of claim 1 wherein the polymerizable resin comprises a resin selected from the group consisting of urethane dimethacrylate (UDMA), diurethane dimethacrylate (DUDMA), polycarbonate dimethacrylate (PCDMA), ethoxylated bisphenol A dimethacrylate (EBPDMA), triethylene glycol dimethacrylate (TEGDMA), polyethylene glycol dimethacrylate (PEGDMA), urethane dimethacrylate (UDMA), hexane dial dimethacrylate (1,6 HDDMA) and polycarbonate dimethacrylate (PCDMA), the condensation product of bisphenol A and glycidyl methacrylate, 2,2'-bis [4-(3-methacryloxy-2-hydroxy propoxy)-phenyl]-propane (BIS-GMA), tetrahydrofurfuryl methacrylate (THFMA), ethoxylated bisphenol A dimethacrylate (EBPADMA) and 1.6-hexanediol dimethacrylate (HDDMA), hydroxyethyl methacrylate (HEMA), and mixtures thereof.

4. The method of claim 1 wherein the resin comprises a mixture of a high-viscosity resin and a low-viscosity resin.

5. The method of claim 4 wherein the high-viscosity resin is selected from the group consisting of BIS-GMA, UDMA, modified BIS-GMA, PCDMA and mixtures thereof.

6. The method of claim 4 wherein the low-viscosity resin is selected from the group consisting of TEGDMA, PEGDMA, HDDMA, HEMA, THFMA and mixtures thereof.

7. The method of claim 1 wherein the ultraviolet light absorber is selected from the group consisting of benzophenones, benzotriazoles and mixtures thereof.

8. The method of claim 7 wherein the benzophenones comprises 2-hydroxy-4-methoxybenzophenone.

9. The method of claim 7 wherein the benzotriazoles are selected from the group consisting of 2-(2'-hydroxy-5'-methylphenyl)benzotriazole and 2-(2-hydroxy-5-tert-octylphenyl)benzotriazole.

10. The method of claim 1 wherein the non-oil containing natural flavoring agent is selected from the group consisting of an oleoresin, essence, extractive, protein hydrolysate, distillate of any product of roasting, heating or enzymolysis, which contains the flavoring constituents derived from a spice, fruit juice, vegetable, vegetable juice, herb, bud, bark, root, leaf and mixtures thereof.

11. The method of claim 1 wherein the non-oil containing natural flavoring agent is selected from the group consisting of cinnamon, ginger, lemon, orange, grape, carob bean, cherry, banana, apple, berry, chicory and cola.

12. The method of claim 1 wherein the artificial flavoring agent is selected from the group consisting of hydrocarbons, alcohols, aldehydes, ketones, esters, phenol ethers, lactones, quinones, organic acids, and mixtures thereof.

13. The method of claim 1 wherein the artificial flavoring agent is selected from the group consisting of anisyl alcohol (caramel), benzyl cinnamate (chocolate), vanillin acetate (vanilla), decyl acetate (orange), 2-methylbutyaldehyde (coffee), allyl propionate (apple), perillaldehyde (cherry), and carvyl acetate (peppermint).

14. The method of claim 1 wherein the curing system is selected from the group consisting of a UV-activated curing system and a visible light-activated curing system.

15. The method of claim 1 wherein the curing system is selected from the group consisting of a benzil, benzoin, benzoin methyl ether, ethyl (4-dimethylamino)benzoate (EDMAB), DL-camphorquinone (CQ), benzil diketones and mixtures thereof.

16. The method of claim 1 wherein the filler comprises a filler selected from the group consisting of an inorganic calcium-containing compound, poly(lactide), poly(glycolide), poly(lactide-co-glycolide), poly(methacrylate), silica, silicate glass, quartz, barium silicate, strontium silicate, barium borosilicate, strontium borosilicate, borosilicate, lithium silicate, amorphous silica, alumina, zirconia, tin oxide, titania and mixtures thereof.

17. The method of claim 16 wherein the inorganic calcium compound is selected from the group consisting of calcium hydroxide, calcium phosphates, tricalcium phosphate, or calcium oxide, ammoniated calcium phosphate, and deammoniated calcium phosphate.

18. The method of claim 1 wherein the sealant composition further comprises one or more additives selected from the group consisting of fluorides, antimicrobial agents, and pigments.

19. A method of sealing a patient's teeth with a sealant comprising:
applying a single-component sealant to a patient's teeth wherein the single-component sealant composition for protecting or sealing teeth comprises:
about 50 to about 98% by weight of a polymerizable resin selected from the group consisting of acrylate, methacrylate, polyamides, polyester, polyolefins, polyimides, polyarylates, polyurethanes, vinyl esters, epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates; and
about 0.01 to 0.5% by weight of a non-oil containing natural flavoring agent selected from the group consisting of an oleoresin, essence, extractive, protein hydrolysate, distillate of any product of roasting, heating or enzymolysis, which contains the flavoring constituents derived from a spice, fruit juice, vegetable, vegetable juice, herb, bud, bark, root, leaf and mixtures thereof, and whereby the flavoring agent is selected based on its detectability wherein the flavoring agent in a cured dental sealant has a scent that is undetectable by a patient after two days of submersion in water at 37° C.; and
curing the sealant.

20. A method of sealing a patient's teeth with a sealant comprising:
applying a single-component sealant to a patient's teeth wherein the single-component sealant composition for protecting or sealing teeth comprises:
about 50 to about 98% by weight of a polymerizable resin selected from the group consisting of acrylate, methacrylate, polyamides, polyester, polyolefins, polyimides, polyarylates, polyurethanes, vinyl esters, epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates; and
about 0.01 to 0.5% by weight of an artificial flavoring agent selected from the group consisting of hydrocarbons, alcohols, aldehydes, ketones, esters, phenol ethers, lactones, quinones, organic acids, and mixtures thereof, and whereby the flavoring agent is selected based on its detectability wherein the flavoring agent in a cured dental sealant has a scent that is undetectable by a patient after two days of submersion in water at 37° C.; and curing the sealant.

21. A method of sealing a patient's teeth with a sealant comprising:

applying a single-component sealant to a patient's teeth wherein the single-component sealant composition for protecting or sealing teeth comprises:

about 50 to about 98% by weight of a polymerizable resin selected from the group consisting of acrylate, methacrylate, polyamides, polyester, polyolefins, polyimides, polyarylates, polyurethanes, vinyl esters, epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates;

about 0.01 to 0.5% by weight of a flavoring agent, wherein the flavoring agent is selected from the group consisting of a non-oil containing natural flavoring agent, an artificial flavoring agent, and mixtures thereof, whereby the flavoring agent is selected based on its detectability wherein the flavoring agent in a cured dental sealant has a scent that is undetectable by a patient after two days of submersion in water at 37° C.;

about 0.01 to about 5% by weight of an ultraviolet light absorber;

about 0.01 to about 5% by weight of a curing system;

optionally up to about 50% by weight of a filler;

wherein the non-oil containing natural flavoring agent is selected from the group consisting of an oleoresin, essence, extractive, protein hydrolysate, distillate of any product of roasting, heating or enzymolysis, which contains the flavoring constituents derived from a spice, fruit juice, vegetable, vegetable juice, herb, bud, bark, root, leaf and mixtures thereof; and wherein the artificial flavoring agent is selected from the group consisting of hydrocarbons, alcohols, aldehydes, ketones, esters, phenol ethers, lactones, quinones, organic acids, and mixtures thereof; and curing the sealant.

22. A method of sealing a patient's teeth with a sealant comprising:

applying a single-component composition sealant to a patient's teeth wherein the single-component sealant for protecting or sealing teeth comprises:

about 50 to about 98% by weight of a polymerizable resin selected from the group consisting of acrylate, methacrylate, polyamides, polyester, polyolefins, polyimides, polyarylates, polyurethanes, vinyl esters, epoxy-based materials, styrenes, styrene acrylonitriles, ABS polymers, polysulfones, polyacetals, polycarbonates, polyphenylene sulfides, polyaryl sulfides, acrylonitrile-butadiene-styrene copolymers, polyurethane dimethacrylates;

about 0.01 to 0.5% by weight of a flavoring agent, wherein the flavoring agent is selected based on its detectability wherein the flavoring agent in a cured dental sealant is selected from the group consisting of a non-oil containing natural flavoring agent, an artificial flavoring agent, and mixtures thereof, whereby the flavoring agent has a scent that is undetectable by a patient after two days of submersion in water at 37° C.;

about 0.01 to about 5% by weight of an ultraviolet light absorber;

about 0.01 to about 5% by weight of a curing system;

optionally up to about 50% by weight of a filler;

wherein the non-oil containing natural flavoring agent is selected from the group consisting of an oleoresin, essence, extractive, protein hydrolysate, distillate of any product of roasting, heating or enzymolysis, which contains the flavoring constituents derived from a spice, fruit juice, vegetable, vegetable juice, herb, bud, bark, root, leaf and mixtures thereof;

wherein the artificial flavoring agent selected from the group consisting of hydrocarbons, alcohols, aldehydes, ketones, esters, phenol ethers, lactones, quinones, organic acids, and mixtures thereof;

wherein the system is selected from the group consisting of a benzil, benzoin, benzoin methyl ether, ethyl (4-dimethylamino)benzoate (EDMAB), DL-camphorquinone (CQ), benzil diketones and mixtures thereof;

wherein the ultraviolet light absorber is selected from the group consisting of benzophenones, benzotriazoles and mixtures thereof; and wherein the filler comprises a filler selected from the group consisting of an inorganic calcium-containing compound, poly(lactide), poly(glycolide), poly(lactide-co-glycolide), poly(methacrylate), silica, silicate glass, quartz, barium silicate, strontium silicate, barium borosilicate, strontium borosilicate, borosilicate, lithium silicate, amorphous silica, alumina, zirconia, tin oxide, titania and mixtures thereof; and curing the sealant.

* * * * *